(12) United States Patent
Dumschat

(10) Patent No.: US 9,914,100 B2
(45) Date of Patent: Mar. 13, 2018

(54) SYSTEM FOR PRODUCING DIALYSIS CONCENTRATE

(71) Applicant: INTERMEDT MEDIZIN & TECHNIK GMBH, Ostrhauderfehn (DE)

(72) Inventor: Christoph Dumschat, Leer (DE)

(73) Assignee: INTERMEDT MEDIZIN & TECHNIK GMBH, Ostrhauderfehn (DE)

( * ) Notice: Subject to any disclaimer, the term of this patent is extended or adjusted under 35 U.S.C. 154(b) by 315 days.

(21) Appl. No.: 14/882,475

(22) Filed: Oct. 14, 2015

(65) Prior Publication Data
US 2016/0107128 A1    Apr. 21, 2016

(30) Foreign Application Priority Data

Oct. 15, 2014 (EP) .................................. 14189052

(51) Int. Cl.
| | |
|---|---|
| *B01F 1/00* | (2006.01) |
| *B01F 5/02* | (2006.01) |
| *A61M 1/16* | (2006.01) |
| *B01F 15/02* | (2006.01) |
| *B01F 5/10* | (2006.01) |

(52) U.S. Cl.
CPC ......... *B01F 1/0038* (2013.01); *A61M 1/1666* (2014.02); *B01F 1/0005* (2013.01); *B01F 1/0022* (2013.01); *B01F 5/106* (2013.01); *B01F 15/026* (2013.01); *B01F 15/0243* (2013.01)

(58) Field of Classification Search
CPC ......... B01F 1/0005; B01F 1/0038; B01F 5/02
USPC ...................................................... 366/163.2
See application file for complete search history.

(56) References Cited

U.S. PATENT DOCUMENTS

| | | | |
|---|---|---|---|
| 2,411,239 A | 11/1946 | Reichel et al. | |
| 3,484,369 A * | 12/1969 | De Dobbeleer | A61M 1/1668 210/321.65 |
| 3,508,656 A | 4/1970 | Serfass et al. | |

(Continued)

FOREIGN PATENT DOCUMENTS

| | | |
|---|---|---|
| CN | 202427370 U | 9/2012 |
| CN | 102946982 A | 2/2013 |

(Continued)

*Primary Examiner* — David Sorkin
(74) *Attorney, Agent, or Firm* — Norman B. Thot

(57) ABSTRACT

A dialysis concentrate production system includes a container and a stationary production system. The container comprises a discharge port and a combined port. The stationary production system comprises a storage container comprising a mixing inlet and an outlet, a delivery pump arranged downstream of the outlet, a first water jet pump arranged downstream of the delivery pump, and a second water jet pump arranged downstream of the delivery pump and parallel to the first water jet pump. The first water jet pump comprises a driving inlet in fluid communication with the delivery pump, a suction port in fluid communication with the combined port, and an outlet. The second water jet pump comprises a driving inlet in fluid communication with the delivery pump, a suction port in fluid communication with the discharge port, and an outlet in fluid communication with the mixing inlet.

10 Claims, 1 Drawing Sheet

(56) References Cited

U.S. PATENT DOCUMENTS

| | | | |
|---|---|---|---|
| 3,515,275 A * | 6/1970 | Bowman | A61M 1/1656 210/180 |
| 3,528,550 A | 9/1970 | Cappelen, Jr. | |
| 4,202,760 A * | 5/1980 | Storey | A61M 1/1656 252/364 |
| 4,734,198 A * | 3/1988 | Harm | A61M 1/1656 210/321.72 |
| 6,361,201 B1 * | 3/2002 | Russell | A61M 1/1656 366/136 |
| 2003/0043688 A1 * | 3/2003 | Peterson | B01F 1/0016 366/137 |
| 2013/0079269 A1 | 3/2013 | Koike et al. | |

FOREIGN PATENT DOCUMENTS

| | | |
|---|---|---|
| DE | 103 13 965 B3 | 10/2004 |
| EP | 2 623 188 A1 | 8/2013 |
| SE | 406 863 B | 3/1979 |

\* cited by examiner

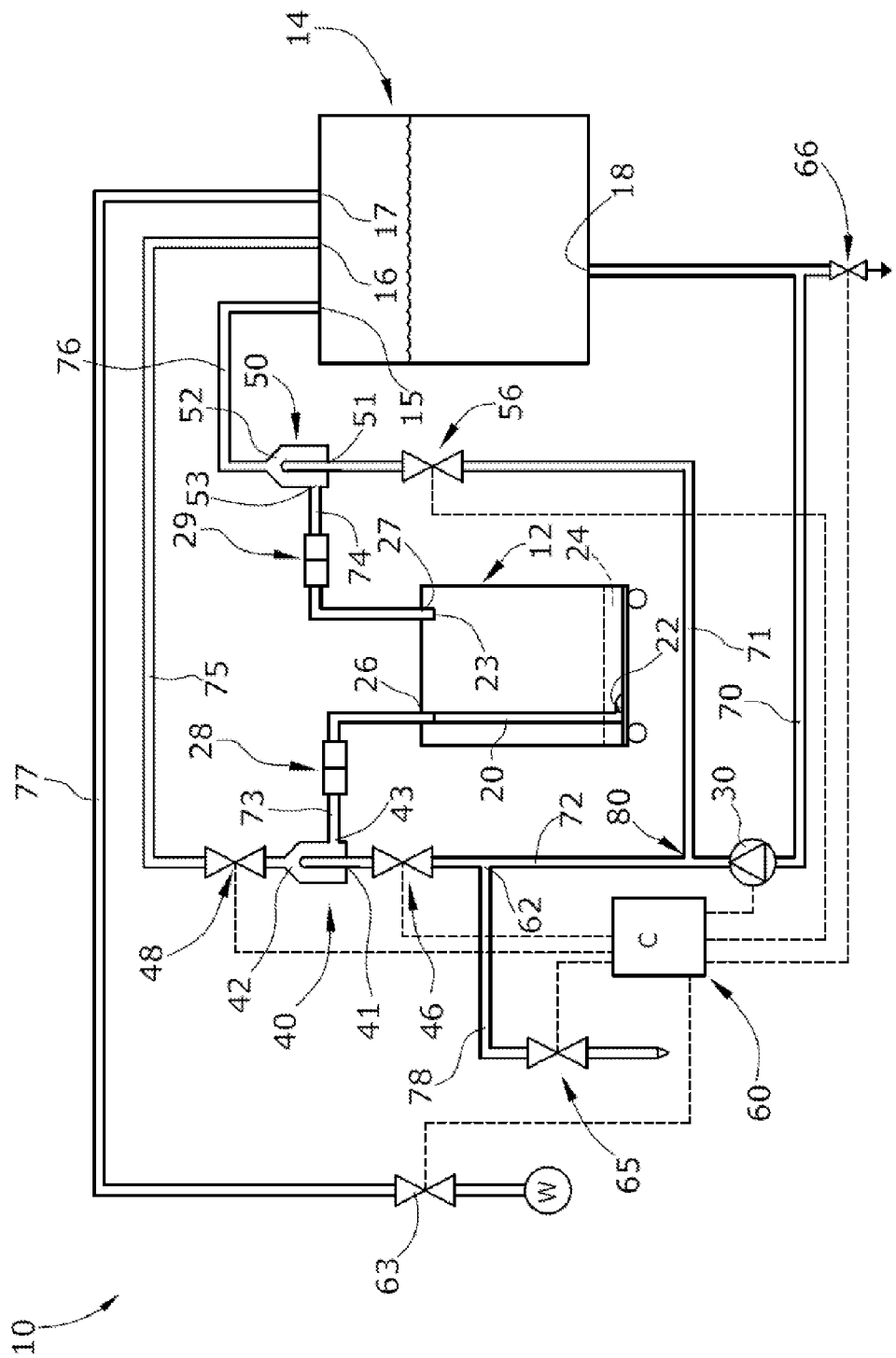

SYSTEM FOR PRODUCING DIALYSIS CONCENTRATE

CROSS REFERENCE TO PRIOR APPLICATIONS

Priority is claimed to European Patent Application No. 14189052.5, filed Oct. 15, 2014. The entire disclosure of said application is incorporated by reference herein.

FIELD

The present invention relates to a dialysis concentrate production system for producing a dialysis concentrate liquid by dissolving a dry concentrate in water, and to a method for producing the dialysis concentrate fluid using the production system.

BACKGROUND

Some 150-200 l of dialysis liquid are usually required to carry out a typical dialysis treatment. The dialysis liquid is generally produced in the dialysis apparatus using two dialysis concentrate liquids and water which are, for example, mixed in a ratio of 1/35. For the production of the dialysis liquid, an alkaline dialysis concentrate liquid, which typically is a sodium hydrogen carbonate solution of a defined concentration, and an acidic dialysis concentrate liquid, in which all other ingredients necessary for the dialysis liquid are contained in the required concentration, are homogeneously mixed with water.

Up to 5 l of acidic dialysis concentrate solution is required to carry out a typical dialysis treatment, with 90% thereof being water. A dialysis concentrate production system has previously been described in DE 103 13 965 B3 where a dry concentrate is homogeneously mixed with water to obtain the dialysis concentrate liquid. The dry concentrate is supplied in a mobile and reusable interchangeable container having two ports for introducing and discharging liquid, respectively. Both ports are connected in situ to a stationary production system which, among others, comprises a so-called storage container, a delivery pump downstream of an outlet of the storage container, two water jet pumps, and a plurality of valves.

The process of producing the dialysis concentrate liquid starts by introducing a precisely measured volume of water into the storage container. By switching shut-off valves in an adequate manner, the water is then pumped from the storage container into the interchangeable container, whereby the dry concentrate is dissolved in the water. As soon as the closed interchangeable container is completely filled with liquid, the liquid flows through a drain at the upper end of the interchangeable container back to the storage container. The liquid is pumped to circulate between the storage container and the interchangeable container and back until the dry concentrate is dissolved completely and homogeneously in the entire liquid volume.

The liquid is pumped under pressure into the interchangeable container and flows under pressure from the outlet to the storage container. The interchangeable container is thus continuously exposed to overpressure and must not leak since significant amounts of liquid may otherwise be lost without being readily noticed. This may also lead to an undesirable change in the concentration of the chemical ingredients of the dry concentrate in the total liquid.

SUMMARY

An aspect of the present invention is to provide a dialysis concentrate production system and a method for producing a dialysate concentration liquid which reduces liquid loss.

In an embodiment, the present invention provides a dialysis concentrate production system for producing a dialysis concentrate liquid by dissolving a dry concentrate in water. The dialysis concentrate production system includes a container configured to be mobile, interchangeable, and to hold the dry concentrate, and a stationary production system. The container comprises a discharge port and a combined port. The stationary production system comprises a storage container comprising a mixing inlet and an outlet, a delivery pump arranged downstream of the outlet, a first water jet pump arranged downstream of the delivery pump, and a second water jet pump arranged downstream of the delivery pump and parallel to the first water jet pump. The first water jet pump comprises a first water jet pump driving inlet, a first water jet pump suction port, and a first water jet pump outlet. The first water jet pump driving inlet is in fluid communication with the delivery pump. The first water jet pump suction port is in fluid communication with the combined port of the container. The second water jet pump comprises a second water jet pump driving inlet, a second water jet pump suction port, and a second water jet pump outlet. The second water jet pump driving inlet is in fluid communication with the delivery pump. The second water jet pump suction port is in fluid communication with the discharge port. The second water jet pump outlet is in fluid communication with the mixing inlet of the container.

BRIEF DESCRIPTION OF THE DRAWINGS

The present invention is described in greater detail below on the basis of embodiments and of the drawing in which:

FIG. 1 schematically shows a dialysis concentrate production system for producing a dialysis concentrate liquid by dissolving a dry concentrate in water.

DETAILED DESCRIPTION

The dialysis concentrate production system of the present invention also comprises a mobile interchangeable container holding the dry concentrate. The interchangeable container has a discharge port via which the liquid leaves the interchangeable container during the mixing process, and a combined port which, during the mixing process, is used both to fill and to empty the interchangeable container. The interchangeable container is substantially gas- and liquid-tight so that it can be subjected to at least a low overpressure without a loss of liquid.

The stationary production system has a storage container with an outlet that can, for example, be arranged at the bottom of the storage container and through which the liquid flows from the storage container. The storage container also has a mixing inlet which can, for example, open into the storage container at the top thereof. The production system also includes a delivery pump downstream of the storage container outlet. The delivery pump can, for example, be designed as an electric displacement pump. A first water jet pump is arranged further downstream of the delivery pump. The first water jet pump has a driving inlet through which the liquid from the delivery pump flows into the water jet pump under pressure. The water jet pump has a suction port in fluid communication with the combined port of the interchangeable container via a corresponding connecting conduit.

A second water jet pump is provided downstream of the delivery pump, the second water jet pump being arranged fluidically in parallel with the first water jet pump. The driving inlet of the second water jet pump is supplied with the pressurized liquid delivered by the delivery pump. The suction port of the second water jet pump is in fluid communication with the discharge port of the interchangeable container. The outlet of the second water jet pump is in fluid communication with the storage container mixing inlet so that the liquid coming from the outlet of the second water jet pump is introduced into the storage container.

The delivery pump thus feeds the driving inlets of the two water jet pumps whose suction ports are in fluid communication with the combined port and the discharge port of the interchangeable port.

The mixing of dialysis concentrate liquid from the dry concentrate in the connected interchangeable container and the defined volume of water in the storage container can be started as soon as the storage container is filled with the defined volume of water. For this purpose, the shut-off valves, to the extent provided, are switched so that the flow path from the delivery pump to the driving inlets of the two water jet pumps is open, but one shut-off valve behind the outlet of the first water jet pump is closed.

As soon as the delivery pump is active, the delivery pump pumps the water flowing from the storage container to the two water jet pumps with approximately the same flow rate and at approximately the same pressure. In the first water jet pump, the water flows through the suction port in the opposite direction and from there through the combined port into the interchangeable container where the dry concentrate is dissolved in the inflowing water. At the same time, the second water jet pump acts as a vacuum pump and thereby evacuates the interchangeable container until the liquid level in the interchangeable container reaches the discharge port. As soon as the liquid level in the interchangeable container reaches the discharge port, the second water jet pump operates as a suctioning liquid pump and draws liquid from the interchangeable container, which flows back from the outlet of the second water jet pump back into the storage container.

The liquid is thereby continuously circulated between the storage container and the interchangeable container. The liquid is pumped into the interchangeable container at a certain overpressure through the first water jet pump and is drawn from the interchangeable container at a certain negative pressure through the second water jet pump. When the counter-pressure in the combined port rises, the flow rate in the first water jet pump decreases so that the flow rate in the second water jet pump correspondingly rises, so that the negative pressure generated by the second water jet pump also rises at the suction port thereof. The two water jet pumps thus control each other.

A static pressure is thereby obtained inside the fluid-tight interchangeable container which is only slightly below or above the atmospheric ambient pressure. Tests have shown that the pressure difference between ambient pressure and the internal pressure in the interchangeable container are in the order of about 0.1 bar.

A practically pressureless mixing phase is realized due to the small pressure difference so that even in the event of leaks in the mobile interchangeable container, the leakage losses caused thereby are very low. This is important because high demands are made on adhering to exact mixing proportions of the dry concentrate in the water. Since the interchangeable container is not exposed to any significant internal overpressure, the container is subjected to less stress, in particular in the region of the seals and passages, so that the durability of the interchangeable container is thereby improved.

In an embodiment of the present invention, the outlet of the first water jet pump can, for example, be in fluid communication with a filling inlet of the storage container. A first shut-off valve is arranged fluidically between the outlet of the first water jet pump and the filling inlet of the storage container so that when the first shut-off valve is closed, the liquid conveyed by the delivery pump is pumped in reverse flow into the interchangeable container through the suction port of the first water jet pump. When the first shut-off valve is open, however, the liquid is drawn from the combined port of the interchangeable container through the suction port of the first water jet pump. The flow direction of the suction port of the first water jet pump is reversed by switching the first shut-off valve.

After the dry concentrate has been dissolved completely and homogeneously in the entire volume of water in the mixing phase, the previously closed first shut-off valve is opened so that in the subsequent collecting phase, all of the system liquid, including the liquid in the interchangeable container, is finally pumped completely into the storage container. The entire mixing process is completed as soon as this is finished so that the interchangeable container can be disconnected and removed.

In an embodiment of the present invention, a second shut-off valve can, for example, be arranged between the driving inlet of the first water jet pump and the delivery pump. During the mixing phase, fluid, i.e., gas or liquid, is drawn from the discharge port of the interchangeable container through the suction port while the second shut-off valve is open. The second shut-off valve is closed during the subsequent collecting phase so that the second water jet pump generates no more negative pressure in the interchangeable container. The second water jet pump is thereby deactivated fluidically during the collecting phase.

In an embodiment of the present invention, the combined port of the interchangeable container opens into a fluid opening at the lowest point of the interchangeable container. It is thereby provided that the interchangeable container is completely emptied during the collecting phase so that no liquid remains in the interchangeable container. This is important since the strict adherence to the predetermined mixing proportion of the dry concentrate in the water would otherwise not be provided.

In an embodiment of the present invention, the discharge port of the interchangeable container can, for example, open in a fluid opening in the upper portion of the interchangeable container and, for example, at the highest point inside the interchangeable container. A maximum flow path length of the liquid is thereby provided within the interchangeable container, thereby promoting the best possible homogeneity of the dissolved dry concentrate in the liquid.

In an embodiment of the present invention, the two water jet pumps can, for example, have an identical technical design. A fluidic branch can, for example, be provided downstream of the delivery pump from which each arm of the branch leads to the respective driving inlet of the two water jet pumps. The two water jet pumps are thus fed symmetrically by the delivery pump, i.e., they are supplied with the same flow rate. Due to the fluidic and structural symmetry of the two water jet pumps, the respective delivery rate is stabilized on approximately the same level. It is thereby provided, in particular during the mixing phase, that the internal pressure in the interchangeable container differs only slightly from the atmospheric ambient pressure.

An embodiment of the present invention will be explained in detail below with reference to the drawing.

FIG. 1 schematically shows a dialysis concentrate production system 10 for producing a dialysis concentrate liquid by dissolving a dry concentrate in water. The production system 10 is formed by a mobile interchangeable container 12 holding a dry concentrate 24 and by a stationary production system having a plurality of components.

The interchangeable container 12 is of a barrel-like shape and is fluidically closed. The interchangeable container 12 may have wheels for transport. The interchangeable container 12 has a discharge port 27 at the top, whose associated inner opening 23 is provided at the highest point within the interchangeable container 12. The interchangeable container 12 also has a combined port 26 at the top which, within the interchangeable container 12, opens into a vertical riser tube 20 at the lower end of which a riser tube opening 22 is provided that is open in a tangential flow direction. The combined port 26 and the discharge port 27 are each associated with a respective connecting coupling 28, 29 via which the interchangeable container 12 is fluidically connected with the production system 10 in a simple manner.

The production system 10 has a so-called storage container 14 with a mixing inlet 15, a collecting inlet 16, and a filling inlet 17 at the top thereof. At its lowest point, the storage container 14 has an outlet 18. The outlet 18 of the storage container 14 is in fluid communication with a delivery pump 30 of the displacement type via an outlet line 70, the delivery pump 30 conveying the liquid from the storage container 14. A fluidic branch 80 is provided downstream of the delivery pump 30, wherein a first branch line 72 leads to a first water jet pump 40 via a third shut-off valve 46, while a second branch line 71 leads to a second water jet pump 50 via a second shut-off valve 56, which second water jet pump 50 is technically identical with the first water jet pump 40.

Each of the two water jet pumps 40, 50 has a respective driving inlet 41, 51, an outlet 42, 53 and a suction port 43, 53. The suction port 43 of the first water jet pump 40 is in fluid communication, via a conduit 73, with the combined port 26 of the interchangeable container 12 or the connecting coupling 28 associated with the combined port 26. The suction port 53 of the second water jet pump 50 is in fluid communication, via a conduit 74, with the discharge port 27 of the interchangeable container 12 or the connecting coupling 29 associated with the discharge port 27. The outlet 52 of the second water jet pump 50 is in fluid communication with the mixing inlet 15 of the storage container 14 via a conduit 76. The outlet 42 of the first water jet pump 40 is in fluid communication with the collecting inlet 16 of the storage container 14 via an interposed first shut-off valve 48 and a conduit 75.

If necessary, water, for example, treated and filtered tap water, flows from a water source W via a fourth shut-off valve 63 and a filling conduit 77 to the filling inlet 17 of the storage container 14.

A flushing branch with a discharge valve 66 is provided in the branch between the storage container outlet 18 and the delivery pump 30, via which flushing branch the storage container 14 can be emptied completely into a drain.

A further fluidic branch 62 is provided between the delivery pump 30 and the third shut-off valve 46, from which branch a delivery conduit 78 with a fifth shut-off valve 65 branches for the purpose of pumping out the ready mixed dialysis concentrate liquid.

The shut-off valves illustrated, the delivery pump 30 and a plurality of (not illustrated) sensors herein, for example, flow sensors, density sensors etc., are read, controlled and monitored by a system control 60 that controls the entire production process.

The production process is as follows:

First, the interchangeable container 12 refilled with dry concentrate 24 is fluidically connected with the production system via the two connecting couplings 28, 29. After the production process has been started subsequently thereto, the system control 60 opens the fifth shut-off valve 63 so that water flows from the water source W into the storage container 14 via the filling conduit 77 and the filling inlet 17. During the filling phase, the delivery pump 30 is not in operation and all other shut-off valves are closed. As soon as the storage container 14 is filled with the defined amount of water, the fifth shut-off valve 63 is closed so that no more water flows.

The filling phase is followed by the mixing phase. For this purpose, the system control 60 opens the third shut-off valve 46 and the second shut-off valve 56 and activates the delivery pump 30. The first shut-off valve 48 remains closed. The first water jet pump 40 is thus operated in reverse flow and the second water jet pump 50 is operated in the suction mode. The delivery pump 30 delivers the water from the storage container to the two water jet pumps 40, 50. Since the first shut-off valve 48 is closed, the water flows in reverse flow through the suction port 43 of the first water jet pump 40 into the mixing inlet 26 of the interchangeable container 12 so that the liquid level in the interchangeable container 12 rises. The water flows tangentially from the riser tube opening 22 so that the powder-like dry concentrate 24 is entrained by the water flow and is dissolved in the water. At the same time, the second water jet pump 50, which first operates as a vacuum pump in this phase creates a certain vacuum/negative pressure so that the interior of the interchangeable container 12 is almost pressureless when compared to the ambient pressure.

As soon as the liquid level in the interchangeable container 12 reaches the container lid, the liquid flows through the discharge 27 and the conduits 74, 76 into the mixing inlet 15 of the storage container 14. In this phase, the second water jet pump 50 operates as a liquid suction pump so that the interior of the interchangeable container 12 is almost pressureless relative to the atmospheric ambient pressure. The total volume of liquid in the system is larger than the filling volume of the interchangeable container 12 so that the liquid is continuously pumped to circulate between the storage container 14 and the interchangeable container 12. A homogenization of all ingredients of the dry concentrate in the liquid is thereby achieved, until the homogeneity is finally high enough for the liquid to be used as a dialysis concentrate liquid. The homogeneity of the liquid is determined, for example, by density sensors and/or in an electrochemical or optical manner.

As soon as the mixing phase is completed, the second shut-off valve 56 is closed and the first shut-off valve 48 is opened. The first water jet pump 40 is then operated in the suction mode, while the second water jet pump 50 is not operating, so that the interchangeable container 12 is pumped completely empty via the suction port 43 of the first water jet pump 40 and the pumped-out liquid is pumped to the collecting port 16 of the storage container 14 via the conduit 75. As soon as the interchangeable container 12 is thus pumped completely empty, the collecting phase is terminated by closing the third shut-off valve 46. Now, the storage container 14 holds the entire amount of dialysis concentrate liquid produced in this manner.

Finally, the dialysis concentrate liquid is pumped from the storage container 14 by opening the fourth shut-off valve 65 so that the dialysis concentrate liquid can be pumped out into a suitable transport container via the delivery conduit 78.

The present invention is not limited to embodiments described herein; reference should be had to the appended claims.

What is claimed is:

1. A dialysis concentrate production system for producing a dialysis concentrate liquid by dissolving a dry concentrate in water, the dialysis concentrate production system comprising:
   a container configured to be mobile, interchangeable, and to hold the dry concentrate, the container comprising a discharge port and a combined port; and
   a stationary production system comprising:
      a storage container comprising a mixing inlet and an outlet,
      a delivery pump arranged downstream of the outlet,
      a first water jet pump arranged downstream of the delivery pump, the first water jet pump comprising a first water jet pump driving inlet, a first water jet pump suction port, and a first water jet pump outlet, the first water jet pump driving inlet being in fluid communication with the delivery pump, and the first water jet pump suction port being in fluid communication with the combined port of the container, and
      a second water jet pump arranged downstream of the delivery pump and parallel to the first water jet pump, the second water jet pump comprising a second water jet pump driving inlet, a second water jet pump suction port, and a second water jet pump outlet, the second water jet pump driving inlet being in fluid communication with the delivery pump, the second water jet pump suction port being in fluid communication with the discharge port, and the second water jet pump outlet being in fluid communication with the mixing inlet of the container.

2. The dialysis concentrate production system as recited in claim 1, wherein,
   the storage container further comprises a filling inlet,
   the dialysis concentrate production system further comprising:
   a first shut-off valve arranged fluidically between the first water pump jet outlet and the filling inlet,
   wherein,
   the first water jet pump outlet is in fluid communication with the filling inlet,
   a fluid is drawn from the combined port via the first water jet pump suction port when the first shut-off valve is open, and
   a liquid is pumped into the combined port via the first water jet pump suction port when the first shut-off valve is closed.

3. The dialysis concentrate production system as recited in claim 1, further comprising:
   a second shut-off valve arranged between the second water jet pump driving inlet and the delivery pump,
   wherein,
   a fluid is drawn from the discharge port through the second water jet pump suction port when the second shut-off valve is open.

4. The dialysis concentrate production system as recited in claim 1, wherein the container further comprises a first fluid opening arranged at a lowest point of the container at an end of the combined port.

5. The dialysis concentrate production system as recited in claim 1, wherein the container further comprises a second fluid opening arranged at a top portion of the container at an end of the discharge port.

6. The dialysis concentrate production system as recited in claim 1, wherein the first water jet pump and the second water jet pump have an identical structure.

7. The dialysis concentrate production system as recited in claim 1, wherein the delivery pump is a displacement pump.

8. The dialysis concentrate production system as recited in claim 1, further comprising:
   a dialysis concentrate liquid delivery conduit arranged to branch fluidically between the delivery pump and the first water jet pump; and
   a third shut-off valve arranged between the dialysis concentrate liquid delivery conduit and the first water jet pump,
   wherein,
   the delivery pump is configured to pump the dialysis concentrate liquid from the storage container into the dialysis concentrate liquid delivery conduit when the third shut-off valve is closed.

9. A method for producing a dialysis concentrate liquid with a dialysis concentrate production system to mix the dialysis concentrate liquid from a dry concentrate and water, the dialysis concentrate production system comprising:
   a container configured to be mobile, interchangeable, and to hold the dry concentrate, the container comprising a discharge port and a combined port;
   a stationary production system comprising:
      a storage container comprising a mixing inlet, a filling inlet, and an outlet,
      a delivery pump arranged downstream of the outlet,
      a first water jet pump arranged downstream of the delivery pump, the first water jet pump comprising a first water jet pump driving inlet, a first water jet pump suction port, and a first water jet pump outlet, the first water jet pump driving inlet being in fluid communication with the delivery pump, and the first water jet pump suction port being in fluid communication with the combined port of the container, and
      a second water jet pump arranged downstream of the delivery pump and parallel to the first water jet pump, the second water jet pump comprising a second water jet pump driving inlet, a second water jet pump suction port, and a second water jet pump outlet, the second water jet pump driving inlet being in fluid communication with the delivery pump, the second water jet pump suction port being in fluid communication with the discharge port, and the second water jet pump outlet being in fluid communication with the mixing inlet of the storage container;
   a first shut-off valve arranged fluidically between the first water pump jet outlet and the filling inlet; and
   a second shut-off valve arranged between the second water jet pump driving inlet and the delivery pump,
   the method comprising:
      filling the storage container with water;
      closing the first shut-off valve;
      opening the second shut-off valve and the third shut-off valve; and activating the delivery pump to dissolve the dry concentrate into the dialysis concentrate liquid and to mix the dialysis concentrate liquid.

10. The method as recited in claim 9, wherein, after mixing the dialysis concentrate liquid, the method further comprises:
closing the second shut-off valve and opening the first shut-off valve.

* * * * *